United States Patent [19]

Desai et al.

[11] Patent Number: 4,816,247

[45] Date of Patent: Mar. 28, 1989

[54] EMULSION COMPOSITIONS FOR ADMINISTRATION OF SPARINGLY WATER SOLUBLE IONIZABLE HYDROPHOBIC DRUGS

[75] Inventors: Narendra R. Desai, Danbury, Conn.; Edward C. Shinal, Old Tappan, N.J.; Madurai Ganesan, Pomona; Eugene A. Carpentier, Spring Valley, both of N.Y.

[73] Assignee: American Cyanamid Company, Stamford, Conn.

[21] Appl. No.: 774,762

[22] Filed: Sep. 11, 1985

[51] Int. Cl.$^4$ .................. A61K 31/02; A61K 31/08; A61K 31/16; A61K 31/40

[52] U.S. Cl. ...................... 424/80; 424/439; 514/938; 514/939; 514/943

[58] Field of Search ............... 424/80, 38, 439; 514/938, 939, 943

[56] References Cited

U.S. PATENT DOCUMENTS

| | | | |
|---|---|---|---|
| 3,172,816 | 3/1965 | Swintosky | 514/943 |
| 3,647,624 | 3/1972 | Evenson | 435/2 |
| 3,991,206 | 11/1976 | Tolman et al. | 424/317 |
| 3,996,934 | 12/1976 | Zaffaroni | 128/268 |
| 4,124,720 | 11/1978 | Wenmaekers | 514/943 |
| 4,125,603 | 11/1978 | Audibert et al. | 514/938 |
| 4,168,308 | 9/1979 | Wretlind et al. | 514/938 |
| 4,340,054 | 7/1982 | Michaels | 128/260 |
| 4,563,354 | 1/1986 | Chang et al. | 514/938 |
| 4,610,868 | 9/1986 | Fountain et al. | 424/1.1 |
| 4,647,586 | 3/1987 | Mizushima et al. | 514/532 |
| 4,670,255 | 6/1987 | Yoshizumi et al. | 424/93 |
| 4,703,062 | 10/1987 | Blackburn et al. | 514/552 |

FOREIGN PATENT DOCUMENTS

| | | |
|---|---|---|
| 1127039 | 7/1982 | Canada . |
| 2113568 | 8/1983 | France . |
| 58/59912 | 4/1983 | Japan . |
| 2105589 | 3/1983 | United Kingdom . |

*Primary Examiner*—Ronald W. Griffin
*Attorney, Agent, or Firm*—R. P. Raymond

[57] ABSTRACT

Lipid emulsion form compositions have been formulated and presented to eliminate adverse injection site reactions associated with the intravenous administration of certain sparingly water soluble, hydrophobic, ionizable drugs in mammals and to provide a solubilized drug form for oral, parenteral or intraarticular administration which enhances drug absorption and the therapeutic efficacy of the drug.

22 Claims, 7 Drawing Sheets

EMULSION COMPOSITIONS FOR ADMINISTRATION OF SPARINGLY WATER SOLUBLE IONIZABLE HYDROPHOBIC DRUGS

BACKGROUND OF THE INVENTION

In times past, emulsion systems have been used as dosage forms, normally for the oral administration of oils, or in the form of topical products or cosmetics. At the present time, emulsions also have utility as parenteral drug delivery systems. L. D. Pelham, Am. J. Hosp. Pharm., 38: 198-208 (1981), reports total parenteral nutrition (TPN) has been one of the most important advances in acute patient care over the past decade. It is a means of providing intravenous nutrition to patients who are unable to absorb nutrients via the gastrointestinal tract. Infused nutrients may include amino acids, dextrose, electrolytes, minerals, vitamins, fatty acids and trace minerals.

As reported by L. D. Pelham in the prior cited reference, intravenous fat emulsions have been commercially available in European countries for over 20 years though their use in the United States has been restricted until recently because of severe and infrequently fatal reactions as reported in the Br. J. Surg., 52: 795-800 (1965) and Drug Intell. Clin. Pharm., 6: 321-30 (1972). Lipomul®, the first intravenous fat emulsion introduced in the United States, was withdrawn in 1965 following several reports of a "fat overloading syndrome" as described in the Br. J. Surg., 52: 291-8 (1965) and Metabolism 6: 815-21 (1957). Intralipid®, distributed by Cutter Laboratories, was approved for use in the United States in 1975. It had previously been used in Europe for years. In 1979, Liposyn®, a second intravenous fat emulsion, was marketed by Abbott Laboratories.

Intralipid® and Liposyn® contain 10% w/v or 20% w/v soybean oil and 10% w/v safflower oil respectively, as a source of polyunsaturated fatty acids. Each product contains 1.2% w/v of purified egg phospholipids as an emulsifier and water is added to make a 10% w/v or 20% w/v emulsion. Until recently only 10% emulsions were available in the U.S. In Europe 20% emulsions constitute the majority of use as reported in Surg. Clin. North Am., 58: 1055-70 (1978). Glycerol, a water-soluble substance, is added to make fat emulsions isotonic, with 2.25% w/v in Intralipid® and 2.5% w/v in Liposyn®. Since fat exerts a minimal osmotic pressure, glycerol contributes twice the osmotic load as an equal weight of glucose, mannitol, or sorbitol according to the N. Engl. J. Med., 297: 1444-52 (1977). Both Intralipid® and Liposyn® have a pH range of 5.5 to 8; emulsified fat particles in Intralipid® and Liposyn® range from 0.1 to 0.5 m in diameter, slightly smaller than endogenous chylomicrons as reported in serveral references, including Metabolism, 27: 1109-27 (1978).

Since the early 1970's most reports in the literature for adverse reactions attributed to fat emulsions related to the use of Intralipid® simply because it was the only commercially available fat emulsion. Similar adverse reactions may be reported for Liposyn® with the passage of time. Intralipid® and Liposyn® appear to have significantly fewer and milder adverse reactions than Lipomul® as reported in Can. Med. Assoc. J., 111: 152-4 (1974) and Liposyn® Research Conference proceedings. North Chicago; Abbott Laboratories (1979). Most serious reports today are associated with excessive doses as reported in Arch. Surg., 111: 1391-3 (1976).

Two types of adverse reactions occur with fat infusions. The first type is usually acute or mild and occurs during the infusion. The second type occurs later with prolonged use of intravenous fat emulsions. The most commonly reported acute reactions include a febrile response, chills and shivering and pain in the chest or back, described in J. Pediatr., 86: 2-16 (1975). Very rapid infusions may cause palpitations, tachypnea, sudden tightness of the chest, wheezing, cyanosis, nausea, pain at injection site, oily taste and headache as reported in Br. J. Surg., 52: 291-8 (1965). During recent years the intravenous fat emulsions which were initially reserved for the provision of essential fatty acids have gained in popularity as a coloric source as described in U.S. Pat. No. 3,169,094 and by M. T. Yeo, et al. in Arch. Surg., 106: 792-6 (1973). As reported by R. Jeppsson and S. Ljungberg in Acta Pharmacal. et. Toxical, 36: 312-20 (1975). Ljungberg and Jeppsson investigated pharmacodynamic effects of using emulsions as vehicles for lipid soluble materials in 1970, '72 and '73. Effects were investigated after parenteral administration of soybean oil emulsions containing various drugs dissolved in the oil phase. The drugs studied were barbituric acids, cyclandelate nitroglycerin and diazepam. The results indicated that the emulsion formulations would be suitable vehicles for lipid soluble drugs intended for intravascular administration, since the pharmacological effects were nearly equal to those found after a water solution of the sodium salts. A prolongation of anesthesia was observed for barbituric acids when administered in the oil phase of a soybean emulsion as compared with a solution of the corresponding sodium salt. The results were explained as a slow release of the drug from the oil particles or, the possibility of a more specific delivery of the drugs to the central nervous system when the drug is contained in oil droplets [R. Jeppsson, Acta pharmaceutica sueccia, 9, 81-90 (1972)]. A commercial diazepam emulsion product has been reported as being available by O. Dardel, et al., Anaesth. Scand., 20: 221-24 (1976). This lipid emulsion formulation was prepared by Vitrum AB, Sweden and shows many similarities to Intralipid®. The new lipid emulsion form was found to significantly reduce the incidence of local side effects involving the venous system and no significant difference in the therapeutic effect of the different preparative forms of diazepam was observed.

SUMMARY OF THE INVENTION

The present invention relates to compositions of matter comprising quick breaking, in vivo, intravenous, intramuscular, intraarticular and/or oral fat emulsion form preparations which incorporate the use of certain saturated or unsaturated aliphatic or aromatic acids, e.g., caproic, capric or oleic acid and aromatic acids, e.g., hydroxy benzoic or cinnamic acids, and the like as a cosurfactant and/or as an ion-pair former [A discussion of the theories and applications of ion-pair formation may be found in the following publications and related references: Naunyn-Schmiedeberg's Arch. Pharmacol. 264: 55≧75 (1969); J. Pharm. Pharmacol. Suppl. 28: 75P (1976); J. Pharm. Pharmacol. 31: 749-753 (1981); and J. Pharm. Pharmacol. 35: 45 (1984).] and which are designed to solubilize certain sparingly water soluble hydrophobic ionizable drugs and certain water insoluble hydrophobic viscous oily liquids and/or those basic drugs which have negative logarithms of ionization constants, i.e., pk's, lower or nearer the physiological pH or, in the case of acidic drugs the drug may be a viscous oily liquid or solid water insoluble hydrophobic acid which may have negative logarithm of the ionization constant or constants, e.g., pk's higher or nearer the physiological pH.

Thus, in the case of acidic drugs (with lower or nearer pk's constants than the physiological pH) or basic drugs (with higher or nearer pk's), when introduced in a physiological environment (e.g. I.V. infusion) they are converted into molecular forms of considerably lowered solubilities. As a result, the drugs precipitate, resulting in localized high accumulation of potentially irritating compounds.

Ionization constants are inherent molecular properties which cannot be changed without making covalent modifications in the structure of a compound. At a somewhat later stage in the history of the preclinical pharmaceutical development of the compound, if covalent changes in the structure are made, the chemical is considered a new chemical entity and thus all the pharmaceutical, pharmacological, toxicological, pharmacokinetic and other biological data have to be repeated. Also many times covalent structure modification results in loss or reduction or complete change in the pharmacological activity.

This invention, describing quick-breaking (or quick drug releasing) emulsion drug delivery liquid system, circumvents the local precipitation of drugs without making convalent modification in the structure of the problem drugs.

Hydrophobic water insoluble acidic drugs may derive their acidic function from the —COOH group, phenolic —OH group, —SO$_3$H group or amino acid groups or similar functional groups which upon losing a proton generate anions or zwitterions. In this case a pharmaceutically acceptable amine such as a glucamine may be employed as an ion-pair former, e.g., N-methyl-D-glucamine and homologs thereof of the formula: R—NH—CH$_2$(CHOH)$_4$CH$_2$OH, where R is hydrogen or alkyl(C$_1$-C$_6$). An example of ion-pair formation between a hydrophobic acidic drug and an amine was accomplished by combining the compound 4-biphenyl acetic acid (a known analgesic and anti-inflammatory agent disclosed in U.S. Pat. Nos. 3,784,704 and 3,991,206) with N-methyl-D-glucamine dissolved in the oil phase of emulsion (vegetable oil, soy or egg lecithin and emulsion stabilizing surfactants) and formulated as an oil in water emulsion. This formulation has been proposed for intramuscular or intraarticular injection. Some of the advantages to be derived from this type of formulation are: to prevent the drug from precipitating as crystals and causing pain at the site of injection or in the tender tissues associated with inflammatory arthritis; to provide a slow sustained release of the drug at the local pathological site; and to prevent initiation of immunological inflammatory responses resembling arthritis. Certain antitumor agents such as bis(2-imidazolen-2-ylhydrazone)-9,10-anthracenedicarboxaldehyde (disclosed in U.S. Pat. No. 4,258,181 and hereinafter referred to as bisanthrene base) and adriamycin base disclosed in U.S. Pat. No. 3,590,028 or the like, are examples of basic hydrophobic drugs which may be solubilized by this procedure. The compound 3-[4,6-bis[(1,1-2,2-tetramethylpropyl)amino]-s-triazin-2-yl]-3-azabicyclo[3.2.2]nonane which has utility as an antiarthritic agent and is disclosed in U.S. Pat. No. 4,261,892 is also a sparingly water soluble hydrophobic ionizable drug and may be successfully formulated with a fat emulsion vehicle as well. This solubilized drug in the emulsified preparation may also be administered by the intravenous route without harmful side effects.

It is contemplated that the emulsion solubilization systems described herein may have application with a number of other drug substances, some of which are known commercial products and others which are reported in the literature, e.g.; Triamterene, a diuretic found in U.S. Pat. No. 3,081,230 (1963 to Smith, Kline & French); Amphotericin B, an antifungal agent: Gold, et al., Antibiot. Ann. 1955–1956, 579; or U.S. Pat. No. 2,908,611 (1959 to Olin Mathieson); Ibuprofen, an anti-inflammatory agent, in U.S. Pat. No. 3,385,886 (1968 to Boots Pure Drug Company Ltd.); Indomethacin, an anti-inflammatory agent, in U.S. Pat. No. 3,161,654 (1964 to Merck & Co.); Terfenadine RMI-9918, an antihistamine without CNS effects, is disclosed in Annual Drug Data Report, 3: 246 (1981) (Richardson-Merrell Inc.); (triphenylphosphoranylidene)carbamic acid, ethyl ester, has an undisclosed pharmaceutical activity, and is disclosed in East German Pat. No. 137,716; the compounds phenyl[7-(4-pyridinyl)pyrazolo[1,5-a]pyrimidin-3-yl]methanone and 2-furanyl[7-(3-pyridinyl)pyrazolo[1,5-a]pyrimidin-3-yl]methanone, which have utility as anxiolytic agents, are disclosed in patent application, Ser. No. 506,966, filed June 23, 1983 by the American Cyanamid Co.; the compound 5-(3-bromophenyl[1,2,4]triazolo[1,5-c]pyrimidin-2-amine, an antiasthmatic agent, in patent application, Ser. No. 518,250, filed July 28, 1983 by the American Cyanamid Co.; and Cisplatin hydrophobic complexes such as 2-hydrazino-4,5-dihydro-1H-imidazole compound with platinum chloride (PtCL$_2$) (1:1) and 5-hydrazino-3,4-dihydro-2H-pyrrole, compound with platinum chloride, both of which are active as antineoplastic agents and are disclosed in patent application, Ser. No. 553,675, filed on Nov. 21, 1983 by the American Cyanamid Co.

Examples of other commercial acidic drugs, which precipitate in varying amounts at the physiological pH upon intravenous infusion, are the following:

TABLE IA

| Trade Mark | Ambient Solution pH | pH beyond which significant precipitation occurs |
| --- | --- | --- |
| Droperidol (dehydrobenzperidol) | 3.24 | 5.83 |
| Thalamonal | 3.44 | 6.00 |
| Dipidolor (piritramide) | 3.97 | 4.50 |
| Phenergan (promethazine) | 5.68 | 6.42 |
| Largactil (chloropromazine) | 5.75 | 6.50 |
| Nozinan (levomepromize) | 4.38 | 6.50 |
| Prazine (promazine) | 4.85 | 7.10 |
| Atarax (hydroxyzine) | 5.60 | 6.40 |
| Inderal (propanolol) | 3.50 | 6.00 |
| Aramine (metaraminol) | 3.60 | 5.80 |
| Persantine (dipyridamole) | 3.12 | 5.10 |
| Eraldin (practolol) | 5.80 | 7.40 |

DETAILED DESCRIPTION OF THE INVENTION

Figure 1:
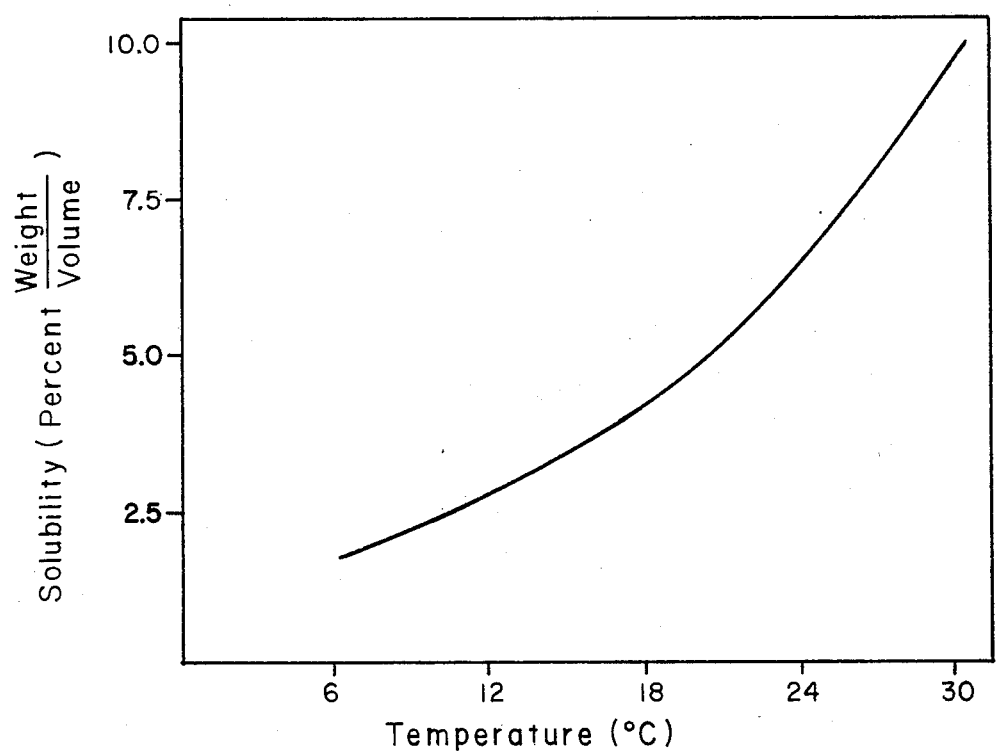
FIG. 1 show solubility of bisantrene in water.

The present invention encompasses the compositions of matter hereinafter to be described and a method of treatment therewith.

In many instances in the treatment of humans or animals with drugs it may be necessary to administer the drug by the intravenous route. Intravenous administration is the quickest and most direct means of drug delivery. However, local intravenous injection site adverse reactions may occur which could be due to: (a) thermodynamically driven local precipitation of a potentially irritating drug in high amounts; (b) inherent quality of the drug to preferentially bind with the injection site tissue and hence cause high local accumulation of the drug, and (c) needle damaged vein; leading to extravasation and then attack by the drug of the exposed tissue.

As reported in Acta Anesthesiologica Belgica, No. 3, 230-240 (October) 1973; even without obvious bacterial contamination, local thrombophlebitis is very common with intravenous infusions or injections. With infusions this problem occurred in approximately 30 percent of the cases studied no matter whether a needle, a metal or plastic cannula was used. Other series showed an incidence of post-infusion thromobophlebitis of 25-30 percent, whereas in 32 percent of the cases the complication symptoms did not appear until after one week. Also findings reported in Drug Intelligence and Clinical Pharmacy, 3, 266 (May) 1977 showed that 33 percent of all IV administered anticancer drugs were associated with the development of thrombophlebitis. Suggested solutions to the problem were directed to (a) consideration of needle or catheter size versus blood vessel diameter, (b) consideration of the density of infused solutions and (c) a new split type needle or catheter.

As previously mentioned, the intravenous route offers a direct and rapid means of drug administration and as reported in a recent article on Extravasation in Drug Intelligence and Clinical Pharmacy, 17, 713 (October) 1983 it is not a simple method, but one that requires special equipment, skilled personnel and close monitoring. One of the hazards of this route is the accidental misdirection of IV fluid and medication from a vein into the interstitial tissue. This could occur by slippage of an IV cannula from a vein into the tissue or when the IV fluid leaks from the vein through a puncture in the vein or around the cannula site. This article reports that extravasation was found to occur in 11 percent of IV treatments administered to children in cases studies and in as many as 22.8 percent of IV treatments in adults studied. Fortunately, most of these mishaps are recognized quickly and little harm results. Although it was determined that a small percentage of cases resulted in tissue damage due to extravasation, damage resulting from extravasation can be severe and can lead to a longer hospital confinement than originally intended. The initial presentation of an extravasation injury depends on the character of the medication and the volume of solution that has entered the interstitial tissue. In its simplest form, extravasation injury can appear as a painful, erythematous swelling surrounding the IV cannula site. If only part of the skin thickness is damaged, the area may appear blistered, with mottling and darkening of the skin. When the full thickness of the skin is damaged, the surface may appear very white and later may develop as a mass of dead tissue.

A review of the problems associated with the prevention and treatment of local toxicities caused by extravasation of cancer chemotherapeutic drugs may be found in Cancer Treatment Reviews, 7: 17-27 (1980). As described in Seminars in Oncology, 9 No. 1, 14–22 (March) 1982; most of the veins used for administration of chemotherapy course between the dermis and subcutaneous fat. Extravasation of toxic drugs can cause a full thickness loss of skin above the affected area. In areas of little subcutaneous fat such as the upper surface of the hand and around joints, severe damage to nerves, tendons and muscle can also occur. Some remedies suggested to reduce the change of extravasation were (a) to use a freely flowing IV line, injecting normal saline before and after a venipuncture injection, (b) avoiding the antecubital fossa and hand, (c) using the proper flow rate and (d) using only the venous side of an arteriovenous fistula. However, it is reported that many cancer patients have such poor veins that occasional extravasation cannot be avoided.

Adverse injection site reactions described below for Adriamycin (Doxorubicin) are common for many drugs, with physiologically inconvenient ionization characteristics leading to precipitation at and/or binding of drugs with local tissues, when given by the parenteral route. On top of this when there is an accidental extravasation, the problems become very severe.

A problem encountered with the intravenous administration of Adriamycin in cancer therapy is reported in Plastic and Reconstructive Surgery, 61: 86–92 (1978). When the drug extravasates into the soft tissues it causes massive tissue necrosis about the site of the attempted intravenous administration. This necrosis develops at a slow rate, continues to increase in severity for several weeks, and does not heal in the usual manner. The resulting ulcers are indolent, and may remain a source of severe pain and functional impairment for many months without healing. Removal of the necrotic area and surrounding tissues containing the extravasated drug is recommended. Skin grafts take poorly if there are small amounts of the drug left in the tissue of the recipient site.

When an aqueous solution of bisantrene dihydrochloride is injected intravenously in mammals a problem which is likely to occur is chemical phlebitis [Cancer Research, 43: 925–29, (February 1983)]. On the basis of available information, it appears that the phlebitis is caused due to precipitation of the drug from the I.V. solution when mixed with venous blood. The occurrence of particles of drug on the surface of the vein results in local high concentrations for extended periods of time and produces irritation.

Figure 2:
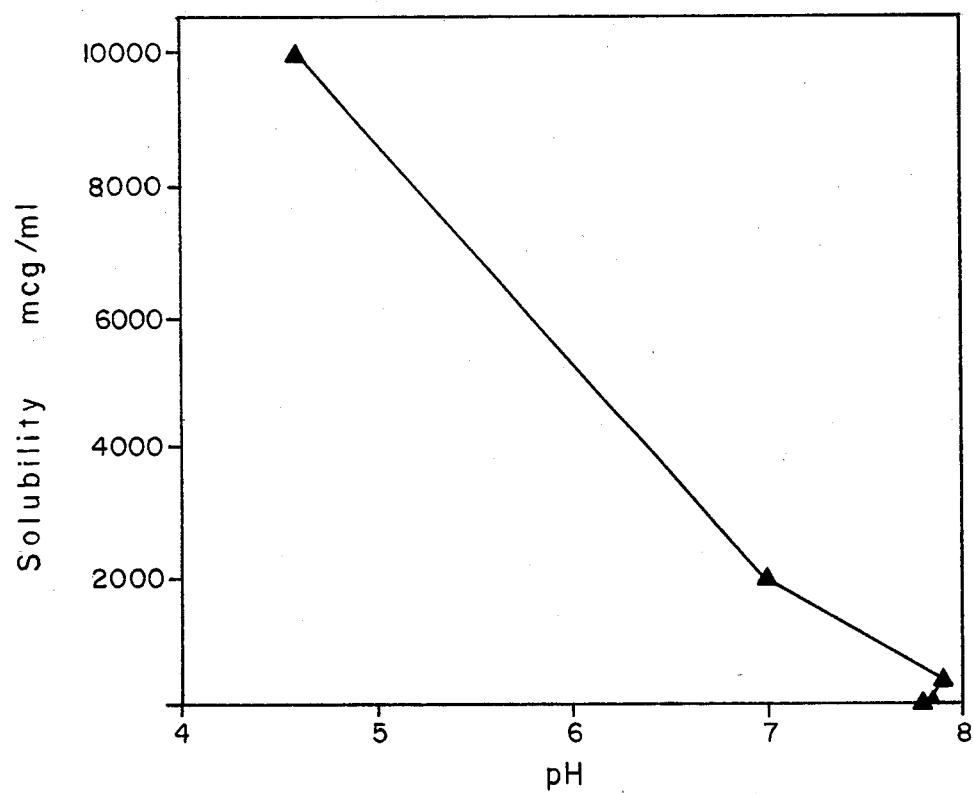
FIG. 2 shows solubility of bisantrene in selected media and biological fluids.

The solubility characteristics of bisantrene which in turn affect precipitation, are very sensitive to temperature changes, pH, and various solutes. For example, FIG. 1 indicates the sensitivity of bisantrene solubility in water at pH 4.5 over a temperature range of 6° C. to 30° C., while Table IB indicates the wide range of its solubility in selected media and biological fluids whose values are plotted in FIG. 2.

TABLE IB

| Solubility of Bisantrene in Selected Media | | |
|---|---|---|
| Medium | pH | Solubility(mcg/ml) |
| 5% Dextrose Solution | 4.6 | 10,000 |
| Normal Saline | 5.5 | 2,000 |
| Whole Blood | 7.9 | 400 |
| Plasma | 7.7–8.2 | 90 |
| Serum | 7.8 | 27 |

It can be seen from the table that bisantrene is quite soluble in media useful as candidates for I.V. infusions such as normal saline and 5% dextrose. In serum and plasma, however due to increase in the pH the solubility drops considerably and this may be the reason that the drug precipitates at the point of infusion. It is also observed that solubility in whole blood is much greater than in plasma and serum. From the drug's solubility characteristics and other information, it appears that the drug eventually partitions into the erythrocytes which then serve as slow release carriers. Thus, if the drug can be kept in solution long enough to allow complete dilution in the entire blood volume, then the partitioning should take place without the intermediate precipitation.

With regard to the antiarthritic compound 3-[4,6-bis[(1,1-2,2-tetramethylpropyl)amino]-s-triazin-2-yl]-3-azabicyclo[3.2.2]nonane, accumulated data indicates that this compound has insignificant solubility in water and is therefore not recommended as a candidate for traditional oral dosage forms such as tablets.

Solubilities were determined in parenterally acceptable solvents and are listed in Table II. Results indicate that the solubility is in the range of 0.5 to 1.5 mg/ml for parenteral solvents. Orally and parenterally acceptable solutions of surfactants and polymers such as Tween 40, 60 or 80, polyethylene glycol 300 or polyvinylpyrrolidone did not increase the solubility by more than 0.5 to 1.0 mg/ml.

TABLE II

| Solubility of Antiarthritic Triazine Compound in Parenterally Acceptable Solvents | |
|---|---|
| Solvent | mg/ml |
| Benzyl Benzoate | 1.3 |
| Propylene Glycol Isostearate | 1.5 |
| Benzyl Alcohol | 0.8 |
| Dimethyl Acetamide | 0.7 |
| Ethanol USP | <0.1 |
| Propylene Glycol | <0.1 |
| 1,3-Butylene Glycol | 0.3 |
| Triacetin | 0.1 |
| Cremophor ® EL | 0.2 |
| Emulphor ® EL-620P | <0.1 |
| Propylene Glycolisostearate | 0.3 |
| Brij ® 35 2% Solution | 0.05 |

Because the antiarthritic triazine compound is a base, organic acids as counter-ions were studied to improve drug solubility. The succinate and cinnamate salts were prepared which increased the solubility of the drug in ethanol. Additional drug complexes were prepared with various organic and inorganic acids. Some acids such as hippuric, suberic and phosphoric gave minor improvements in drug solubility in water. Preliminary findings of candidate dosage forms indicated: (a) parenteral absorption of the drug was negligible and (b) oral absorption was slightly better, however, about 90% of the compound was excreted in the feces. The inherent insolubility of the drug appears to be responsible, to some extent, for the preceding results. In order to overcome the drug insolubility problem one of the objectives considered was to design a dosage form which would improve drug absorption when given by intravenous, intramuscular or intra-articular injection.

An oil in water emulsion delivery system provides an advantageous solution to formulation and delivery problems of hydrophilic, ionizable sparingly water soluble drugs.

1. Local high concentration contact of the drug with blood component and tissue material could be minimized.
2. Containment of the drug in the oil phase of the oil in water emulsion with a controlled rapid release would allow the drug to travel away from the injection site without being precipitated.
3. The apparent limiting drug solubility in vivo (blood) could be increased in the proper emulsion formulation.
4. The localized immobilization of the drug at the injection site, because of its inherent property of precipitation at, or binding with the tissue reduces the bioavailability of potentially toxic drug. By having a biodegradable barrier effect of the emulsion drug immobilization is eliminated, thus increased bioavailability would reduce the minimum effective dose and increase the therapeutic index.
5. A considerable reduction in the cardiac uptake of the drug may result.

The following emulsion associated characteristics are acknowledged to be essential factors to be considered when formulating the desired product:

1. All ingredients must be non-toxic and acceptable for parenteral administration;
2. All emulsion particles should be 5 microns or less (preferably in submicron range) in diameter otherwise they may obstruct the lung capillaries;
3. The emulsion should not aggregate on standing.
4. 
   (a) The emulsion should be stable to the extent needed to carry the drug substantially away from the in vivo injection site, and thus presumably, reduce local site reactions.
   (b) However, the emulsion as a particle should not remain intact long enough to be selectively deposited in the liver and other reticuloendothelial system organs. Selective uptake in these organs is the fate of other particulate delivery systems such as microspheres, liposomes, and routine emulsions.
5. The fat emulsion must withstand radiation sterilization and furthermore it is desirable that it endures wide temperature fluctuations near room temperature.
6. The fat emulsion shall withstand long time storage without breaking, creaming or floculation.
7. A final demand is that the fat emulsions should be of a composition that should not have any adverse pharmacological influence on blood pressure and circulation and other physiological functions.

It has now been determined by us that by a suitable selection of a drug, form fats, emulsifiers, surfactants, cosurfactants, bacteriostats, preservatives, antioxidants and solvents, emulsion systems as carriers for lipid id soluble drugs can be provided which can be supplied to mammals without side reactions.

The characteristic features of the novel emulsion system formulae of the present invention are derived from the variuos ingredients and combinations of ingredients therein, namely those which are encompassed by and included under the following categories: 1. an oleaginous vehicle or oil phase, 2. the active ingredient, 3. a surfactant or emulsifier, 4. a co-surfactant or auxilary emulsifier, 5. an ion-pair former, 6. a toxicity modifier or cryoprotectant (optional), 7. an antioxidant (optional), 8. a bacteriostat or preservative (optional), 9. an emulsion stabilizer and creaming preventor (optional) and 10. water.

The oil phase (1) may comprise of from about 1% to about 50% of the main formula, (a) naturally occurring vegetable oils, e.g., refined sesame oil, peanut oil, olive oil, safflower oil, soybean oil and the like or an oleaginous vehicle such as benzyl benzoate. (b) Semisynthetic mono, di or triglycerides utilizedd individually or in mixtures thereof, e.g., rac-glyceryl-1-monopalmitin, rac-glyceryl-1-monoolein, 1,2-dipalmitin, 1,3-dipalmitin, trimyristin, tripalmitin, tristearin, triolein, trielaidin, trilinolein, triheptadecanoic, and the like or fractionated or synthetic oils which may be exemplified respectively by Miglyol ® 810 and 812, a mixture of caprylic and capric triglycerides manufactured from fractionated coconut oil Dynamit Nobel Chemicals, Sweden, and Neobee ® M5 a fractionated triglyceride of coconut oil origin that has been reconstituted to provide an alcohol soluble oil, manufactured by the Drew Chemical Corp., Boonton, N.J.

(2) The active ingredient may be a sparingly water soluble hydrophobic ionizable drug, a water insoluble hydrophobic viscous oily liquid and/or those which have negative logarithms of the ionization constants i.e., pk's near the physiological pH.

The surfactants (3) may consist essentially of both water soluble and water insoluble types such as (a) natural lecithins or phospholipids derived from egg or soy sources and called egg or soy phosphatides, e.g., egg lecithin, egg phosphatidly ethanolamine, phosphatidic acid, plant monogalactosyl diglyceride (hydrogenated) or plant digalactosyl diglyceride (hydrogenated) and the like; (b) synthetic lecithins such as dihexanoyl-L-$\alpha$-lecithin, dioctanoyl-L-$\alpha$-lecithin, didecanoyl-L-$\alpha$-lecithin, didodecanoyl-L-$\alpha$-lecithin, ditetradecanoyl-L-$\alpha$-lecithin, dihexadecanoyl-L-$\alpha$-lecithin, dioctadecanoyl-L-$\alpha$-lecithin, dioleoyl-L-$\alpha$-lecithin, dilinoleoyl-L-$\alpha$-lecithin, $\alpha$-palmito, $\beta$-oleoyl-L-$\alpha$-lecithin, L-$\alpha$-glycerophosphoryl choline and the like; (c) synthetic surfactants based on glycerine or sorbitol, e.g., sorbitan triisostearate, triglycerol diisostearate or triglycerol pentaoleate and the like, or those based on polyoxyethylated hydrocarbons or vegetable oils, e.g., Cremaphor ® EL or RH40 and the like, Emulphor ® EL-620P or EL-719 and the like or Arlacel ® 186 and the like. Materials such as pluronic F-68, egg lecithin, soy lecithin and the like and certain $C_6$-$C_{20}$ saturated or unsaturated aliphatic acids may selectively be employed as a cosurfactant (4). The above saturated or unsaturated aliphatic acids may also function individually as an ion-pair former (5), that is, they are capable of forming a tight ion-pair bond with an appropriate water insoluble hydrophobic ionizable basic drug. Thus the drug may be both bound and solubilized within the oil phase of an oil in water emulsion delivery system. Cosurfactants (4) and ion-pair formers (5) may be selected from saturated or unsaturated aliphatic or aromatic acids such as, caproic, enanthic, caprylic, capric, lauric, palmitic, stearic, arachidonic, arachidic, oleic, linoleic, linolenic hydroxy benzoic, cinnamic acids and the like. For acidic drugs pharmaceutically acceptable amines such as glucamine and homologs thereof may be used as ion-pair formers.

It is known that various stages or types of ion-pairs dissociate into individual ions in the presence of high polarity or high solvating media such as water, aliphatic alcohols and aqueous organic solvents. To keep both the ions in the tight ion-pair form, low polarity media are required and those are provided by the emulsion oil phase described in (1). These ion-pairs convert the drug into amphipathic molecules and thus function as cosurfactants in the stabilization of emulsions in vitro. One of the most important characteristics of this parenteral emulsion delivery system is in vitro stability of the product on the shelf. However, once injected, in vivo destabilization of emulsion occurs, which in turn provides for quick release of the drug.

A cryoprotectant or tonicity modifier (6) such as glycerol, lactose, mannitol sorbitol and the like is optional and may be employed to provide protection against freezing and also serve as a means to establish and maintain a suitable osmotic pressure in the aqueous phase. The use of an antioxidant (7) is also optional and a material such as dl-$\alpha$-tocopherol may be included in the formulation for this purpose. Should sterility be a problem bacteriostats or preservatives (8) such as benzyl alcohol may be employed. In all cases the completed drug form must be sterile and must be stable under the conditions of manufacture and storage and must be preserved against the contaminating action of microorganism such as bacteria and fungi.

In the selection of the oleaginous vehicle or oil, surfactant and co-surfactant or emulsifier and auxiliary emulsifier, care should be taken to avoid selection of components which will interfere or chemically react with the hydrophobic drug. For example, certain preservatives, such as BHT and BHA, are commonly contained in oil products, and such preservatives may react with hydrophobic drugs, such as bisantrene base. Accordingly, use of oils, or any other component of the emulsion formulation of the present invention having such additives or impurities should be avoided.

The in vitro or shelf-life stability of an emulsion formulation as a carrier of water insoluble ionic or nonionic hydrophobic drug depends (in addition to emulsion constituents) on the molecular structure and shape of the drug. The characteristics of surface film (formed by the emulsion contituents) which is exposed to aqueous cap of the oil in water emulsion droplet dictate the stability of emulsion through its sum total of all the molecular interactions with water. Many times the drug is part of the surface film and thus major portion of drug molecule is also exposed to the aqueous cap. Thus, if an insertion of a drug molecule in the surface film destabilizes the emulsion then hydrophilic or hydrophobic surfactants or polymers as emulsion stabilizers (9), e.g., Emulphor ® EL-620P, Emulphor EL-719, PVP, or variety of Pluronic ® block co-polymers are used. By judicious selection of the type and amount of surfactants or polymers, the surface film of the emulsion can be custom modified for a particular drug.

All particulate liquid or solid (emulsions, liposomes, vesicles, lipid dispersions, polymer drug conjugates; solid microspheres or nanospheres) systems when used as carriers for drugs, on intravenous infusion are selectively taken up in higher concentrations (as compared to the general circulation) by the reticuloendothelial (RES) organs such as liver, spleen etc. For the desired pharmacological effect if uniform distribution of a drug in the systemic circulation is required for potentially toxic drugs or antineoplastic drugs, this is a distinct disadvantage. An advantage of the present invention can be ascribed to the built-in design of in vivo, quick breaking nature of the emulsion or alternatively quick releasing nature of the drug from the carrier system. As a result, the RES organs do not recognize this drug carrier system as a typical particulate system. Thus, the selective uptake of the drugs by the RES does not happen or is diminished when the drugs are solubilized in the emulsion systems described. The quick breaking nature of the emulsion or the quick releasing nature of the drug from the carrier system is achieved in our invention by a choice of ion-pair forming components, e.g., aliphatic or aromatic acids for basic drugs or aliphatic or aromatic amines for acidic drugs. The following is the sequence of events illustrated by an example of Bisantrene base which is a basic drug.

Bisantrene base is insoluble in water, oils, oil phase of emulsions or preformed commercial, nutritional emulsions such as Intralipid ® and Liposyn ®. When Bisantrene base forms an ion-pair with oleic acid the solubility of Bisantrene increases in oils or oil phases of emulsions. Additionally, Bisantrene-oleate ion-pair acts as a surfactant, becomes part of an interfacial emulsion film and stabilizes the emulsion in vitro. This fact is illustrated by findings that the same emulsion formulation without Bisantrene does not have a long shelf-life.

Bisantrene-oleate ion-pair formation, like typical ion-pairs, is a reversible equilibrium phenomenon. The are only stable in low dielectric (or polarity) media such as oils or hydrophobic polymers and solvents. If we do not include the ion-pair in the low polarity oil phase of emulsion, it would dissociate into Bisantrene and oleic acid and precipitate when put in water.

Aliphatic acids and to some extent aromatic acids are bound by plasma proteins and lipoproteins in blood, e.g., nine molecules of oleic acid are bound with one molecule of typical plasma protein. Thus, when Bisantrene emulsion delivery system is infused by the intravenous route, the surface film of the emulsion containing Bisantrene-oleate ion-pair is attacked by plasma proteins; and due to multiple oleic acid binding nature of the proteins, the proteins act as a sink for oleic acid. The equilibrium as shown below is shifted to the right.

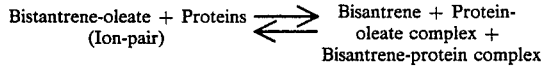

Bistantrene-oleate + Proteins (Ion-pair) ⇌ Bisantrene + Protein-oleate complex + Bisantrene-protein complex The net result of this in vivo interactions is that the drug is released from emulsion. Also the release is proportional to the extent of interaction of emulsion with blood constituents and thus is controlled and gradual. This phenomenon enables subsequent binding of drug with plasma proteins and red blood cell membranes without precipitation at the injection site. Also, as a result of plasma protein dictated dissociation of the Bisantrene-oleate ion-pair, the emulsion stabilizing surfactant property of the ion-pair is lost. By the binding of emulsion phospholipids with the lipids, lipoproteins and proteins in plasma, the emulsion is gradully broken before it reaches the liver. In the case of acidic drugs, solubilized in the emulsion delivery system after forming ion-pairs with glucamines or suitable aromatic amines, a very similar release mechanism in vivo holds.

The invention will be described in greater detail in conjunction with the following specific examples.

Example 1

Preparation of an Emulsion Drug Delivery Vehicle Containing 2 mg/ml Bisantrene Base An amount of bis(2-imidazolin-2-ylhydrazone)-9,10-anthracenedicarboxaldehyde (bisantrene base) equivalent to 2.000 g of pure material was added to 30.000 g of oleic acid USP in a 50 ml erlenmeyer flask with stirring. The mixture was warmed in a water bath at 50°-60° C. for twenty minutes with stirring to complete solution. The flask was removed from the water bath. Then 10.000 g of Emulphor ® EL-620P and 16.000 g of super refined sesame oil was added and the entire mixture was stirred until a homogenous solution resulted whch was called the "oil phase".

To a 29.7 mg amount of dl-α-tocopherol USP was added 564 mg of the preceding oil phase with stirring. A 14.5 mg amount of the above described dl-α-tocopherol mixture was added to 3.0 g of the herein above described oil phase in a scintillation vial. This material was mixed by magnetic stirring until solution was complete, then 46.7 ml of Intralipid ® 20% (Intravenous Fat Emulsion, Cutter Medical, Cutter Laboratories) was added slowly with constant stirring. The resulting emulsion was then sonified for five seconds.

After standing at room temperature for 6 days a slight creaming of the emulsion was observed that disappeared with gentle shaking.

Example 2

Preparation of an Emulsion Drug Delivery System Containing 5 mg/ml Bisantrene Base

| Ingredient | Amount % W/V |
|---|---|
| Bisantrene Base | 0.5 |
| Oleic Acid | 4.0 |
| Emulphor ® EL-620P | 1.0 |
| Soybean Oil | 10.0 |
| Soy Lecithin 95% P.C. | 1.6 |
| dl-α-Tocopherol | 0.05 |
| Glycerine U.S.P. | 2.25 |
| Water for Injection | qs |

(1) A 22.4 g amount of soy lecithin was cut into thin shavings and dissolved in 140 g of soybean oil by stirring under nitrogen and warming in a water bath at 50°-60° C. for approximately 2 hours. (2) An amount of bisantrene base equivalent to 7.000 g of pure material was dissolved in 56.0 g of oleic acid N.F. by stirring and warming in a water bath at 65°-70° C. under nitrogen. (3) A 700 mg amount of dl-α-tocopherol U.S.P. was dissolved in 14.0 g of Emulphor ® El-620P with stirring under nitrogen. The products of steps 1, 2 and 3 were combined in a 2L erlenmeyer flask and stirred and swirled under nitrogen while adding 800 ml of water for injection (WFI) in 80 ml aliquots. Then a solution of 200 ml of WFI containing 31.50 g of glycerine U.S.P. was added to the flask with vigorous swirling. The resulting emulsion was quantitatively transfered to a 2L graduated cylinder and the volume was adjusted to exactly 1400 ml with WFI. The cylinder was stoppered and shaken vigorously. The resulting emulsion was sonicated for 10-15 seconds in 80-100 ml increments using a Branson Sonifier Driver (Branson Instruments Inc., Stamford, CT) at a direct current setting of 6-7 amperes. The pooled sonified material was then homogenized in a Gaulin homogenizer (Gaulin Corp., Everett, MA) at 8000 psi, three times in succession. The homogenized material was then dispensed as 50 ml aliquots into 100 ml vials which were capped and labled.

Example 3

Preparation of an Emulsion Drug Delivery System Containing 2 mg/ml Bisantrene Base

| Ingredient | Amount % W/V |
| --- | --- |
| Bisantrene Base | 0.2 |
| Oleic Acid N.F. | 1.2 |
| Emulphor ® EL-620P | 1.0 |
| Soybean Oil (super refined) | 10.0 |
| Soy Lecithin 95% P.C. | 1.2 |
| dl-α-Tocopherol U.S.P. | 0.01 |
| Glycerine U.S.P. | 2.25 |
| Water for Injection | qs 1000 ml |

(1) A 28.8 g amount of soy lecithin was cut into thin shavings and dissolved in 240 g of super refined soybean oil by stirring under nitrogen and warming at 50°–55° C. in a water bath. (2) A 2.684 g amount of bisantrene base was dissolved in 14.4 g of oleic acid N.F. by warming at 70°–75° C. and stirring under nitrogen. (3) A 0.24 g amount of dl-α-tocopherol U.S.P. was dissolved in 24.0 g of Emulphor ® EL-620P with stirring under nitrogen. Then a 112 g amount of the mixture from step 1 was combined with 14.237 g of the mixture from step 2 and 10.1 g of the mixture of step 3 in a tared 2L erlenmeyer flask. The stirred material (which was identified as the "complete oil phase") was placed into a 42° C. walk-in incubator. A 22.5 g amount of glycerine U.S.P. was added to 150 ml of water for injection with stirring, this mixture was also placed in the 42° C. incubator. In addition, about 750 ml of water for injection in a suitable container was equilibrated at 42° C. in the incubator. Also equilibrated was a 2 liter graduated cylinder and stopper.

After all the components were equilibrated at 42° C. in the incubator, approximately 500 ml of the water for injection was added to the 2 liter tared erlenmeyer flask containing the "complete oil phase". The water was added in 6–8 portions with constant swirling over an interval of about 2 minutes. The herinabove described glycerine/water mixture was added to the emulsion in three portions with constant swirling, then the entire emulsion mixture was transferred to the 2 liter graduated cylinder, shaken vigorously, then brought to volume with water for injection and shaken again.

The entire emulsion mixture was homogenized in an Eppenback Homo-Mixer (Gifford-Woods Co., Hudson, NY) for approximately 3 minutes. Then the mixture was passed through a Gaulin homogenizer in the following manner. The mixture was passed through the apparatus at a pressure of 8,000 psi, three times in succession followed by still another pass at a pressure of 4,000 psi. The final homogenate was then monitered for particle size by photomicrographic examination and showed particles generally of about 1.0μ in size.

The emulsion was then sterile filtered in a conventional manner using a 0.45μ cartridge, under nitrogen, at a pressure of 4 psi. The product was aseptically dispensed as 50 ml aliquots into 100 ml vials. The vials were capped and crimped aseptically, then were labled and contained the product as a light yellow emulsion.

Example 4

Preparation of an Emulsion Drug Delivery System Utilizing Intralipid ® 20% and Containing 2 mg/ml Bisantrene Base

| Ingredient | Amount % W/V |
| --- | --- |
| Bisantrene Base | 0.2 |
| Oleic Acid U.S.P. | 1.2 |
| Emulphor ® EL-620P | 1.0 |
| Sesame Oil (super refined) | 1.6 |
| dl-α-Tocopherol U.S.P. | 0.002 |
| Soybean Oil | 19.2 * |
| Egg Lecithin | 1.152 * |
| Glycerine U.S.P. | 2.16 * |
| Water for Injection | qs |

*derived from Intralipid ® 20%

Preparation of the "Oil Phase"

An amount of Bisantrene Base equivalent to 2.400 g was slowly added to 14.400 g of Oleic Acid U.S.P. with magnetic stirring over a one hour period at room temperature. Then 12.000 g of Emulphor ® 620P was added and stirring was continued for 2 hours. The resulting mixture was warmed to about 50° C. in a water bath and 19.200 g of super refined Sesame Oil was added with stirring for 30 minutes. The 24.0 mg of dl-α-tocopherol was added and the entire mixture was warmed at 45°–55° C. and stirred for an additional 3 hours and 40 minutes to give the completed "oil phase".

When a 4.002 g amount of the above "oil phase" is diluted to 100 ml with Intralipid ® 20%, (20% I.V. Fat Emulsion from Cutter Medical) and the mixture is mixed vigorously and sonified for five seconds the product of the Example is obtained.

Example 5

Preparation of an Emulsion Drug Delivery System Containing 2 mg/ml Bisantrene Base

| Ingredient | Amount % W/V |
| --- | --- |
| Bisantrene Base | 0.2 |
| Oleic Acid U.S.P. | 0.8 |
| Hexanoic Acid | 0.1 |
| Soybean Oil (super refined) | 10.0 |
| Soy Lecithin 95% P.C. | 1.2 |
| dl-α-Tocopherol U.S.P. | 0.01 |
| Polyvinylpyrrolidone Type N.P.-K30 | 0.1 |
| Glycerine U.S.P. | 2.25 |
| Water for Injection | qs |

(1) An amount of bisantrene base equivalent to 1.68 g was slowly added to a mixture of 6.000 g of oleic acid U.S.P. and 0.750 g of hexanoic acid under nitrogen in a 25 ml s erlenmeyer flask with stirring, in a water bath, at 60°–70° C.

(2) An 8.400 g amount of soy lecithin was shaved and added to 70.00 g of soybean oil under nitrogen in a 125 ml s erlenmeyer flask, warmed at 55°–60° C. in a water bath. The mixture was stirred and when the soy lecithin was dissolved 70 mg of dl-α-tocopherol was added. Stirring was continued until solution was complete.

(3) A 13.50 g amount of glycerine U.S.P. was dissolved in water for injection (WFT) and diluted to 100 ml.

(4) A 600 mg amount of Polyvinylpyrrolidone (PVP) type N.P.-K30 was dissolved in 300 ml of water for injection.

The following items were placed in a 42° C. walk-in incubator and allowed to equilibrate to that temperature: the bisantrene base, oleic acid and hexanoic acid mixture of step 1 (8.43 g); the soy lecithin, soybean oil and dl-α-tocopherol mixture of step 2 (78.47 g); the glycerine solution of step 3 (10 ml); the PVP solution of step 4 (300 ml); 250 ml of WFI, a one liter s graduated cylinder and stopper and a one liter erlenmeyer flask.

In the incubator a 6.74 g amount of the mixture from step 1 was combined with 67.26 g of the mixture of step 2 in the one liter erlenmeyer flask with swirling, then the PVP solution of step 4 (300 ml) was added in 4–5 increments of 60–75 ml each, over about a two minute interval. Then 100 ml of WFI was added rapidly in two 50 ml aiquots while swirling, followed by the glycerine solution of step 3. The entire mixture was then transfered to the one liter graduated cylinder and brought to mark at 600 ml with WFI. The mixture was shaken well and while warm was homogenized in an Eppenback Homo-Mixer for 3 minutes at a 750 watt variable voltage transformer (Variac ®) setting of 80. The resulting emulsion was passed through a Gaulin homogenizer four times in succession at a pressure of 8,000 psi. Then the emulsion is filtered through a 0.45 Pall filter and dispensed as 50 ml aliquots into 100 ml vials.

Example 6

Preparation of an Emulsion Drug Delivery System Containing 2 mg/ml Bisantrene Base

| Ingredient | Amount % W/V |
| --- | --- |
| Bisantrene Base | 0.2 |
| Oleic Acid U.S.P. | 1.0 |
| Hexanoic Acid | 0.1 |
| Soybean Oil (super refined) | 10.0 |
| Soy Lecithin 95% P.C. | 1.2 |
| dl-α-Tocopherol U.S.P. | 0.01 |
| Polyvinylpyrrolidone Type N.P.-K30 | 0.1 |
| Glycerine U.S.P. | 2.25 |
| Water for Injection | qs |

(1) An amount of bisantrene base equivalent to 1.680 g was slowly added to a mixture of 7.500 g of oleic acid U.S.P. and 0.750 g of hexanoic acid under nitrogen in a 25 ml s erlenmeyer flask with stirring, in a water bath, at 55°–60° C.

(2) Identical to step 2 in Example 5.

(3) Identical to step 3 in Example 5.

(4) Identical to step 4 in Example 5.

The following items were placed in a 42° C. walk-in incubator and allowed to equilibrate to that temperature: the bisantrene base, oleic acid and hexanoic acid mixture of step 1 (9.930 g); the soy lecithin, soybean oil and dl-α-tocopherol mixture of step 2 (78.470 g); the glycerine solution of step 3 (100 ml); the PVP solution of step 4 (300 ml); 250 ml of WFI, a one liter s graduated cylinder and stopper and a one liter erlenmeyer flask.

In the incubator a 7.942 g amount of the mixture from step 1 was combined with the entire mixture of step 2 (67.260 g) in the one liter erlenmeyer flask with swirling (75.202 g), then the PVP solution of step 4 (300 ml) was added in 4–5 increments of 60–75 ml each, over about a two minute interval. Then 100 ml of WFI was added rapidly in two 50 ml aliquots while swirling, followed by the glycerine solution of step 3. The entire mixture was then transfered to the one liter graduated cylinder and brought to mark at 600 ml with WFI. The mixture was shaken well and immediately, while warm was homogenized in an Eppenback Homo-Mixer for 3 minutes at a 750 watt variable voltage transformer (Variac ®) setting of 80. The resulting emulsion was passed through a Gaulin homogenizer as follows: The 600 ml of emulsion volume was recycled through the apparatus for 4¼ minutes at 8,000 psi. Then passed through once more at 8000 psi. The material was prefiltered using a millipore filter, then sterile filtered through a 0.45μ Pall filter and aseptically dispensed as 50 ml aliquots into 100 ml vials.

Example 7

Preparation of a Placebo for an Emulsion Drug Delivery System Containing Intralipid ® 20%

| Ingredient | Amount % W/V |
| --- | --- |
| Oleic Acid U.S.P. | 1.2 |
| Emulphor ® EL-620P | 1.0 |
| Sesame Oil (super refined) | 1.6 |
| dl-α-Tocopherol U.S.P. | 0.002 |
| Soybean Oil | 19.2 |
| Egg Lecithin | 1.152 * |
| Glycerine U.S.P. | 2.16 |
| Water for Injection | qs |

*derived from Intralipid ® 20%

The ingredients were formulated as described in Example 4, with the exculsion of bisantrene base.

Example 8

Preparation of a Placebo for an Emulsion Drug Delivery System Used for Higher Concentrations of Drug (Bisantrene Base)

| Ingredient | Amount % W/V |
| --- | --- |
| Oleic Acid U.S.P. | 4.0 |
| Emulphor ® EL-620P | 1.0 |
| Soybean Oil | 10.0 |
| Soy Lecithin 95% P.C. | 1.6 |
| dl-α-Tocopherol U.S.P. | 0.05 |
| Glycerine U.S.P. | 2.25 |
| Water for Injection | qs |

The ingredients were formulated as described in Example 2, with the exculsion of bisantrene base.

Example 9

Preparation of an Oral Emulsion Drug Delivery System Containing 10 mg/ml of Antiarthritic Drug

| Ingredient | Amount % W/V |
| --- | --- |
| 3-[4,6-Bis[(1,1-2,2-tetramethyl-propyl)amino]-s-triazin-2-yl]-3-azabicyclo[3.2.2]nonane | 1.0 |
| Oleic Acid | 1.2 |
| Hexanoic Acid | 0.250 |
| Emulphor ® EL-620P | 1.0 |
| Soybean Oil | 10.0 |
| Soy Lecithin-Centrolex P | 1.6 |
| dl-α-Tocopherol | 0.05 |
| Glycerin U.S.P. | 2.25 |
| Water for Injection | qs |

(1) An amount of 3-[4,6-bis[(1,1-2,2-tetramethyl-propyl)amino]-s-triazin-2-yl]-3-azabicyclo[3.2.2]nonane equivalent to 12.000 g was dissolved in a mixture of 14.400 g of Oleic acid U.S.P. and 3.000 g of hexanoic acid by stirring and warming in a water bath.

(2) A 22.400 g amount of soy lecithin (Centrolex ® P) was shaved and added to 140.000 g of super refined soybean oil. The mixture was warmed at 55°–60° C. in a water bath with stirring until solution was complete.

(3) A 600 mg amount of dl-α-tocopherol was dissolved in 12.000 g of Emulphor ® EL-620P as described in step 2 above.

To a one liter erlenmeyer flask was added 24.50 g of the mixture from step 1, 116.00 g of the mixture from step 2 and 10.50 g of the mixture from step 3. This material was stirred and warmed at 55°–60° C. in a water bath, then 500 ml of water for injection was added with constant swirling followed by a solution of 22.50 g of glycerine diluted to 200 ml with water for injection. The preceding mixture was transfered to a 2 liter s graduated cylinder and brought to mark at 1000 ml with WFI. The material was shaken well then was homogenized in an Eppenback Homo-Mixer for 5 minutes and gave a white emulsion.

Example 10

Preparation of an Emulsion Drug Delivery System Containing 10 mg/ml of 4-Biphenyl Acetic Acid for Intramuscular and/or Intraarticular Use

| Ingredient | Amount % W/V |
| --- | --- |
| 4-Biphenyl Acetic Acid | 1.0 |
| N—Methyl-D-glucamine | 0.92 |
| Soybean Oil (super refined) | 7.00 |
| Soy Lecithin 95% P.C. | 1.00 |
| Benzyl Alcohol | 0.60 |
| Glycerine U.S.P. | 4.50 |
| Water for Injection | qs |

(1) A 4.00 g amount of 4-biphenyl acetic acid was stirred and mixed with 3.68 g of N-methyl-D-glucamine and 40 ml of 3A alcohol under nitrogen until a clear solution was obtained. The solution was concentrated in vacuo to remove all of the 3A alcohol. A total of 5.76 g of the above clear concentrate was transferred to a one liter s erlenmeyer flask and stored under nitrogen.

(2) A mixture of 28.00 g of soybean oil, 4.00 g of soy lecithin and about 50 ml fo petroleum ether was dissolved by stirring under nitrogen. The solution was concentrated in vacuo to remove all of the petroleum ether. Then 2.4 g of benzyl alcohol was added to the residue with stirring to give a clear solution.

(3) A 13.50 g amount of glycerine U.S.P. was dissolved in water for injection and diluted to about 60 ml.

(4) A 25.80 g amount of the solution of step 2 was transfered to the one liter s erlenmeyer flask containing 5.76 g of the clear concentrate in step 1.

The following items were placed in a 42° C. walk-in incubator and allowed to equilibrate to that temperature: the flask of step 4 containing the mixture of materials from step 1 and step 2 (31.56 g); the flask from step 3 containing the glycerine/water mixture; a flask containing in excess of 200 ml of WFI; and a 500 ml s graduated cylinder.

In the incubator, while swirling the contents of the flask from step 4, was added slowly about 180 ml of WFI over a 2 minute period. Then with continued swirling was added in a similar manner the glycerine/water mixture from step 3. The entire emulsion was then transfered to the 500 ml s graduated cylinder and the volume was brought to 300 ml with WFI. The cylinder was stoppered and shaken vigorously. The resulting emulsion was sonicated and homogenized as described in Example 2.

Example 11

Preparation of a Two Component Oil Phase for Emulsion Delivery System Used to Increase the Oral Absorption of Drug Component A

| Ingredient | Amount % W/V* |
| --- | --- |
| Emulphor ® EL-620P | 1.0 |
| Soybean Oil | 20.0 |
| Soy Lecithin 95% P.C. | 1.2 |
| dl-α-Tocopherol | 0.05 |

*This composition applies when diluted to 100 ml with water for injection to make an oil/water emulsion.

Component B

| Ingredient | Amount % W/V |
| --- | --- |
| Oleic Acid | 1.2 |

To make 100 g of complete oil phase the desired amount of 3-[4,6-bis[1,1-2,2-tetramethylpropyl)amino]-s-triazin-2-yl]-3-azabicyclo[3.2.2]nonane is added to 5.117 g of component B with mixing for approximately 30 minutes or until the drug is dissolved.

To the above mixture is added 94.883 g of component A with stirring at 50° C. in a water bath until a clear oil phase for emulsion results.

When this combined two component oil phase is administered orally to mammals an emulsion is formed in situ due to the natural action of the digestive system.

Example 12

Preparation of an Emulsion Drug Delivery System Containing 2 mg/ml of Bisantrene Base

| Ingredient | Amount % W/V |
| --- | --- |
| Bisantrene Base | 0.224* |
| Oleic Acid | 0.700 |
| Hexanoic Acid | 0.100 |
| Soybean Oil U.S.P. | 7.000 |
| Soy Lecithin 95% | 1.200 |
| Benzyl Alcohol | 0.900 |
| dl-α-Tocopherol | 0.010 |
| Glycerin U.S.P. | 2.25 |
| Water for Injection | q.s. |

*Amount required to give 0.200% w/v of pure drug.

(1) An amount of bisantrene base equivalent to 2.200 g of pure material was slowly added to a stirred mixture of 7.700 g of oleic acid, 1.100 g of hexanoic acid and 5.6573 g of benzyl alcohol, in a flask, under nitrogen, immersed in a water bath maintained at 55°–60° C. Stirring was continued until complete solution was achieved in about one hour.

(2) A mixture of 77.000 g of soybean oil U.S.P., 110 mg of dl-α-tocopherol and 4.2427 g of benzyl alcohol under nitrogen was warmed and stirred in a flask immersed in a water bath maintained at 40°–45° C. Then 13.200 g of soy lecithin was shaved and added to the mixture and stirring was continued until solution was complete, about 35 minutes.

(3) A 28.125 g amount of glycerine U.S.P. was weighed into a one liter s graduated cylinder, then the graduated cylinder was placed in a 42° C. walk-in incubator and allowed to equilibrate to that temperature. The glycerine was dissolved in water for injection (WFI) equilibrated at 42° C. and brought to mark with WFI.

(4) A 15.383 g amount of the mixture of step 1 was combined with an 85.957 g amount of the mixture from step 2 and swirled in a ≵ 1000 ml graduated cylinder. The cylinder was then placed in the walk-in incubator and allowed to equilibrate. Then 800 ml of the glycerine solution from step 3 was added and the final volume was brought to 1000 ml using WFI. The mixture was shaken well and was homogenized with the aid of a Microfluidizer TM 110 (Microfluidics Corporation, Division of Biotechnology Development Corporation, Newton, MA 02164) at a nitrogen presssure of 80-100 psi to reduce the particle size of the emulsion. The particle size distribution was determined at a wavelength of 632.8 nanometers with a NICOMP Model 200 submicron particle sizer (Pacific Scientific, HIAC/Royco Instruments Div., Smithtown NY 11787) and was found to be in the range of 0.2 to 0.5 microns.

Alternatively, the emulsion may be homogenized by passage through a Gaulin homogeizer as described in Example 5.

Example 13

Preparation of an Emulsion Drug Delivery System Containing 2 mg/ml of Bisantrene Base (with chloroform)

| Ingredient | Amount % W/V |
|---|---|
| Bisantrene Base | 0.224* |
| Oleic Acid | 0.700 |
| Hexanoic Acid | 0.100 |
| Soybean Oil U.S.P. | 7.000 |
| Soy Lecithin 95% | 1.200 |
| Benzyl Alcohol | 0.900 |
| dl-α-Tocopherol | 0.010 |
| Glycerin U.S.P. | 2.25 |
| Water for Injection | q.s. |

*Amount required to give 0.200% w/v of pure drug.

(1) An amount of bisantrene base equivalent to 2.200 g of pure material, 7.700 g of oleic acid, 1.100 g of hexanoic acid and 5.6573 g of benzyl alcohol in a flask, under nitrogen, was solubilized by the addition of 20-40 ml of chloroform with swirling. The resulting solution was subjected to evaporation in vacuo at 30° C. to remove the chloroform, leaving a clear solution of the ingredients.

(2) Then the procedure of Example 12 was continued by following steps 2, 3, and 4 to conclusion.

A comparison of representative formulae of our new emulsion drug delivery systems for bisantrene base with known commercial intravenous fat emulsion products is shown in Table III. It is anticipated that the new emulsion systems described in Table III will find application with other known water insoluble hydrophorbic ionizable drug forms such as Adriamycin, Amphotericin B, Indomethacin, Terfenadine, Promethazine, Chlorpromazine, Hydroxyzine and the like as hereinabove described in Table IA.

TABLE III

Comparison of Known Intravenous Fat Emulsions and New Emulsion Drug Delivery Systems for Bisantrene

| Component % W/V | Intralipid ® | Liposyn ® | Lipomul ® | Emulsion 1 (Ex. 2) | Emulsion 2 (Ex. 3) | Emulsion 3 (Ex. 4) | Emulsion 4 (Ex. 5) | Emulsion 5 (Ex. 6) |
|---|---|---|---|---|---|---|---|---|
| Soybean Oil | 10 | | | 10 | 10 | 19.2 | 10 | 10 |
| Safflower Oil | | 10 | | | | | | |
| Cottonseed Oil | | | 15 | | | | | |
| Super Refined Sesame Oil | | | | | 5 | 1.6 | | |
| Oleic Acid | | | | 4.0 | 1.2 | 1.2 | 0.8 | 1.0 |
| Hexanoic Acid | | | | | | | 0.1 | 0.1 |
| Polyvinylpyrrolidone Type NP-K30 | | | | | | | 0.1 | 0.1 |
| Soybean Phosphatides Soy Lecithin | | | 2.5 | 1.6 | 1.2 | | 1.2 | 1.2 |
| Egg Phosphatide Egg Lecithins | 1.2 | 1.2 | | | | 1.15 | | |
| Pluronic F-68 | | | 0.3 | | | | | |
| Glycerol (Glycerine) | 2.25 | 2.5 | | 2.25 | 2.25 | 2.16 | 2.25 | 2.25 |
| Emulphor ® EL-620P | | | | 1.0 | 1.0 | 1.0 | | |
| dl-α-Tocopherol | | | | 0.05 | 0.01 | 0.002 | 0.01 | 0.01 |
| Dextrose | | | 4 | | | | | |
| Bisantrene Base | | | | 0.5 | 0.2 | 0.2 | 0.2 | 0.2 |
| Water for Injection | 100 | 100 | 100 | Q.S. | Q.S. | Q.S. | Q.S. | Q.S. |

The emulsin drug delivery system formulation of Emulsion 3 in Table III was tested in two species of animals, for peripheral vein irritation in order to determine the occurrence of local injection site adverse reactions. Also tested was a 1.0 mg/ml solution of bisantrene hydrochloride in 5% dextrose/water and a composition of the Emulsion 3 vehicle without bisantrene base. The two species of animals used were rabbits and dogs. The formulations were given intravenously in a peripheral vein using a Butterfly infusion set (Becton, Dickinson Co., Inc., Rutherford, N.J). The marginal ear vein was used in the rabbit and the saphenous or the cephalic vein of the leg was used in the dog.

The formulations were given below by slow intravenous infusion using a Sage syringe pump (Sage Instruments, Orion Research Inc., Cambridge, Ma.) over a 2 hour period. The animals were restrained but unanesthetized during the infusion. After the infusion, the animals were returned to their cages and offered food. The animals were sacrificed one day after the infusion.

Figure 3:
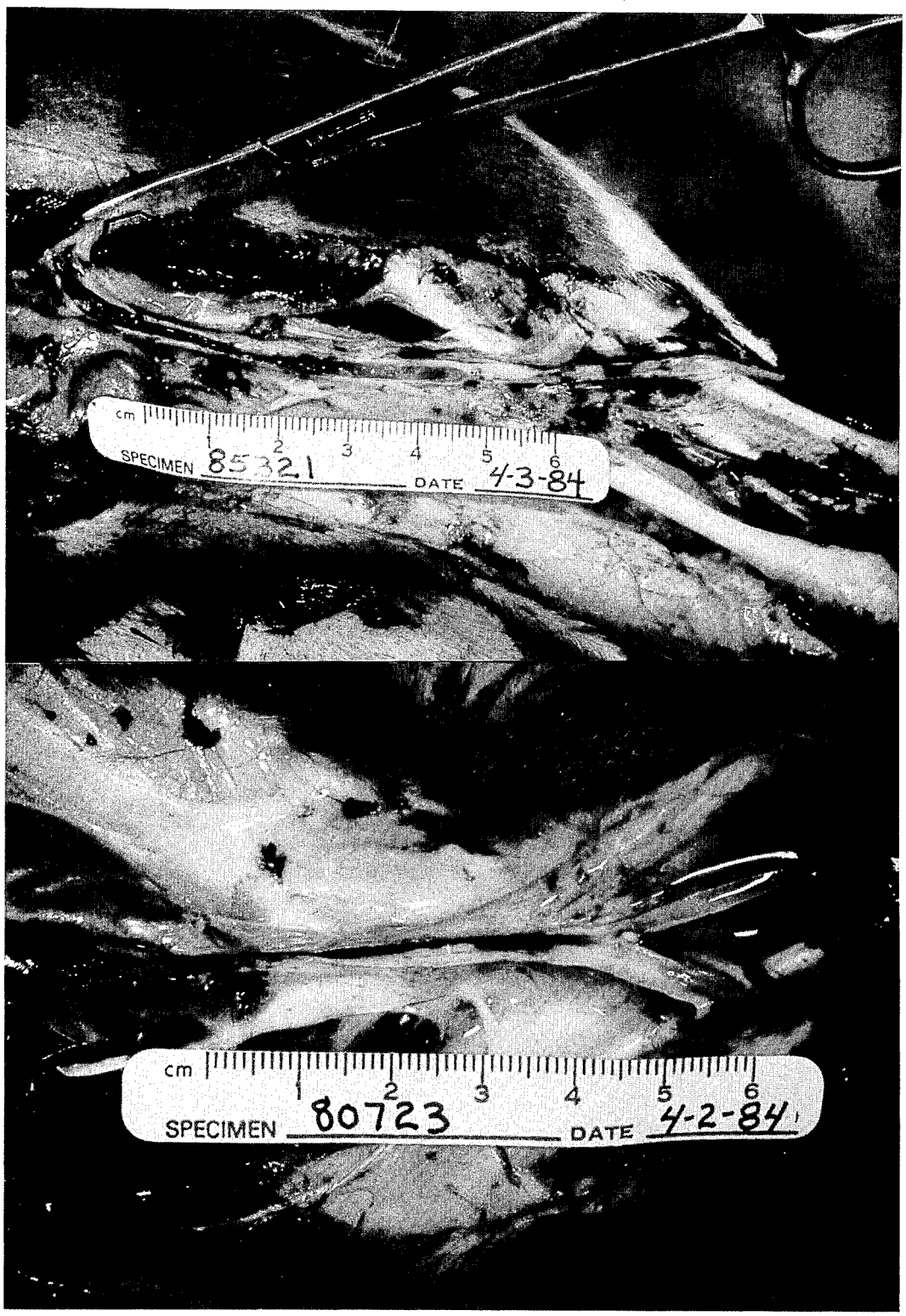
FIG. 3A is a photograph of a dog vein.
FIG. 3B is a photograph of a dog vein.
Figure 4:
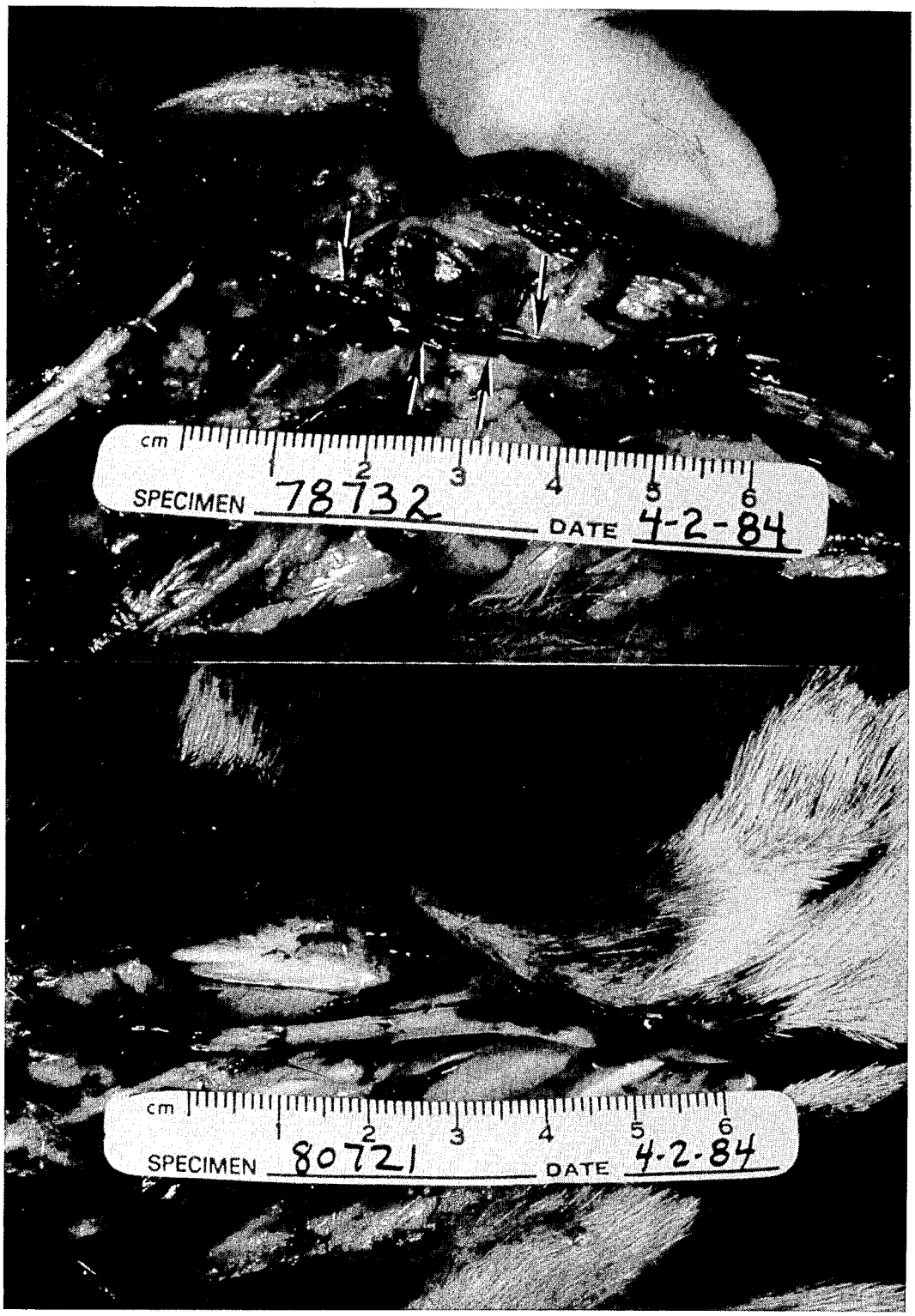
FIG. 4A is a photograph of a dog vein.
FIG. 4B is a photograph of a dog vein.
Figure 5:
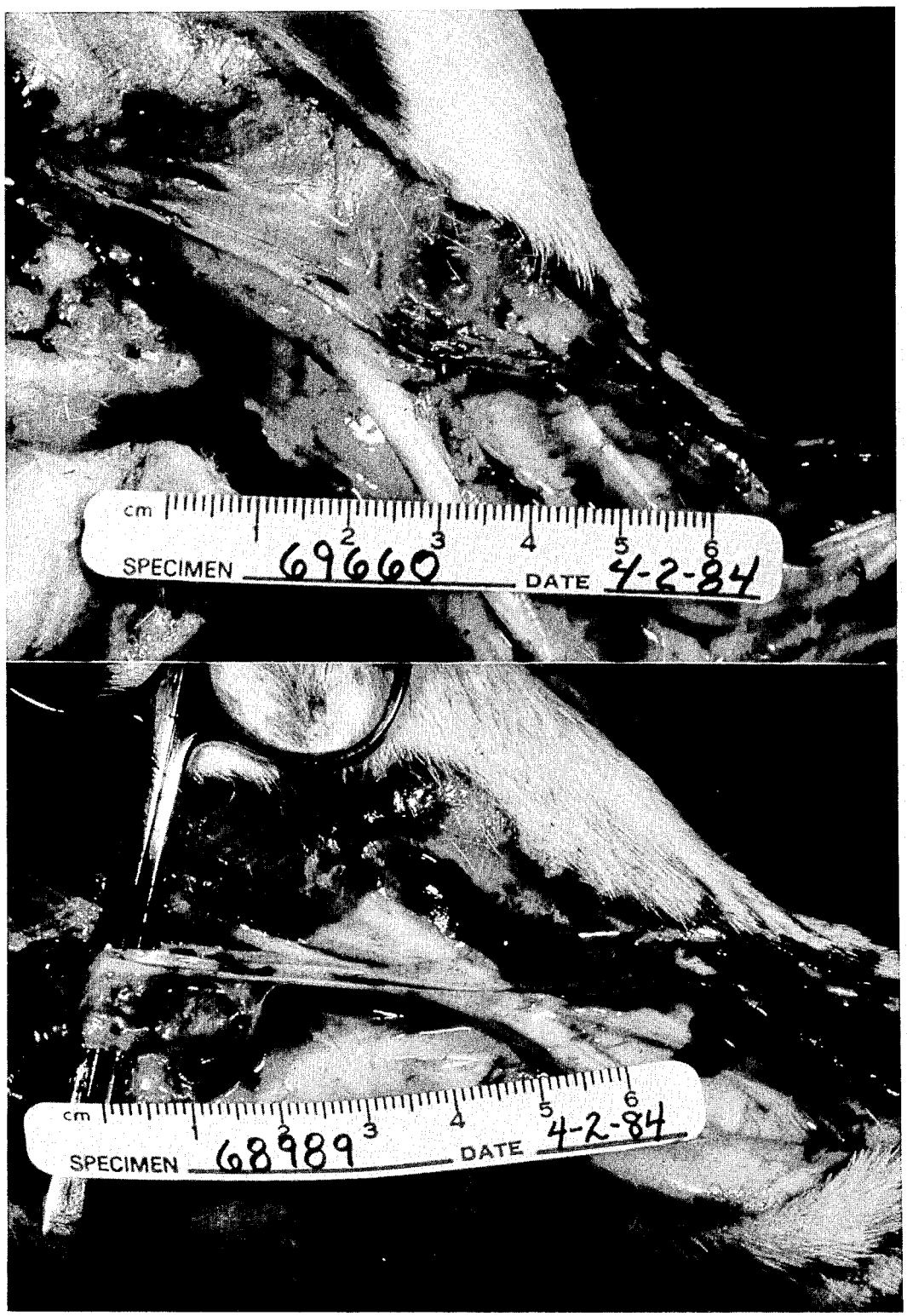
FIG. 5A is a photograph of a dog vein.
FIG. 5B is a photograph of a dog vein.

At sacrifice, the infused vein was opened from the point of infusion and cardiad for several centimeters. The condition of the vein, its intima and the surrounding parenchyma, as well as the presence or absence of orange-yellow material and/or clots in the vein, were recorded in Tables IV and V. Comparative results show conclusively that when bisantrene base in an emulsin drug delivery system was infused into the marginal ear vein of rabbits and the peripheral vein of dogs the vascular-lumen was not affected by the yellow or yellow-orange deposits which result when bisantrene hydrochloride in 5% dextrose/water for injection was infused in the same manner. FIGS. 3, 4 and 5 are comprised of representative photographs of the opened peripheral veins of dogs as hereinabove described and verify the findings stated above.

pointed by the arrows and is offered in comparison with dog specimen 80721, FIG. 4B (bottom photograph) in which only 5% dextrose/WFI was infused into the animals vein.

FIG. 5A (top photograph) dog specimen 69660, was infused with bisantrene base in the Emulsion 3 formula in Table III. The photograph shows that the vascular-lumen of the peripheral vein of the dog was not affected by any yellow-orange deposits and is offered in comparison with dog specimen 68989 FIG. 5B (bottom photograph), in which only Emulsion vehicle alone was infused.

A study was designed to compare the effects of bisantrene base when administered to dogs in an emulsion formula by intravenous infusion in the peripheral vein versus the effects of bisantrene hydrochloride when administered in a dextrose/water vehicle in the same manner. A total of 40 animals were used, one half male and one half female. The animals were divided into 4 groups consisting of 5 male and 5 female animals in each group. All Group I animals were treated with 5% dex-

TABLE IV

Comparative Toxicity Data of the Intravenous Infusion of an Emulsion Formulation with Bisantrene Base, Emulsion Vehicle Without Bisantrene Base and Bisantrene Hydrochloride in 5% Dextrose/Water in the Marginal Ear Vein of Rabbits
Gross Postmortem Findings

| Vehicle | Sex | External | | | Subcutaneous | | | Vascular Lumen | |
|---|---|---|---|---|---|---|---|---|---|
| | | Reddened | Swollen | Yellow Deposit | Hemorrhage | Edema | Yellow Deposit | Blood Clot | Yellow Deposit |
| Bisantrene HCl in 5% Dextrose/Water | F | + | ++ | + | − | ++ | ++ | ++ | + |
| | M | − | − | − | − | + | − | − | + |
| Emulsion #3 Vehicle Without Bisantrene Base | F | ++ | − | − | ++ | + | − | − | − |
| | M | − | − | − | − | +− | − | − | − |
| Emulsion #3 with Bisantrene Base | F | ++ | + | − | ++ | − | − | ++ | − |
| | M | ++ | + | − | + | + | − | − | − |

+ = Positive or present.
− = Negative or absent.

TABLE V

Comparative Acute and Local Toxicity Data of the Intravenous Infusion of an Emulsion Formulation with Bisantrene Base, Emulsion Vehicle Without Bisantrene Base and Bisantrene Hydrochloride in 5% Dextrose/Water in the Peripheral Vein of Dogs
Gross Postmortem Findings

| Vehicle | External | | | Vascular-Lumen | | |
|---|---|---|---|---|---|---|
| | Red or Grey Discoloration | Swelling | Yellowish Discoloration | Blood Clot | Yellow-Orange Deposit | Yellow Color of Intima |
| Bisantrene HCl in 5% Dextrose/Water | − | − | − | ++ | +++ | − |
| | + | ++ | − | +++ | +++ | + |
| Emulsion #3 Vehicle Without Bisantrene Base | + | ++ | − | + | − | − |
| | + | − | − | − | − | − |
| | − | − | − | − | − | − |
| Emulsion #3 with Bisantrene Base | + | +++[a] | + | − | − | − |
| | + | +++[b] | + | ++ | − | − |
| | − | − | − | − | − | ± |
| | − | − | − | − | − | ± |

[a]Extravasation of compound during infusion.
[b]Extravasation of compound during infusion.

In FIG. 3A (top photograph) dog specimen 85321, was infused with bisantrene hydrochloride in 5% dextrose/WFI. The photograph clearly shows the yellow-orange deposit in the vascular-lumen of the peripheral vein of the dog. In FIG. 3B (bottom) photograph, dog specimen 80723 was infused with bisantrene base in the Emulsion 3 formula in Table III. The photograph shows that the vascular-lumen was devoid of the aforesaid deposits.

In FIG. 4A (top photograph) dog specimen 78732, was infused with bisantrene hydrochloride in 5% dextrose/WFI. The photograph again clearly shows the yellow-orange deposits in the vascular-lumen as pintrose/WFI vehicle alone. Group II animals were treated with 2.0 mg/ml bisantrene hydrochloride in 5% dextrose/WFI at a dose of 10 mg/kg or 340 mg/m² with an infusion time of approximately 2 hours each for both the vehicle alone and the vehicle with bisantrene hydrochloride. Group III animals were treated with the emulsion vehicle of Example 3 without bisantrene base present and Group IV animals were treated with the emulsion of Example 3 at a dose of 10 mg/kg or 340 mg/m² also with an infusion time of approximately 2 hours each for the emulsion vehicle alone and the vehicle with bisantrene base. All groups were dosed on the same day with doses administered and every 21 days for a total of three doses.

Clinical signs observed in the animals during the course of the study include: During the intravenous infusion with bisantrene hydrochloride in 5% dextrose/WFI and with the vehicle alone none was apparent, however with the bisantrene emulsion and the emulsion vehicle alone some transient erythema, intravascular hemolysis and hemoglobinuria was observed; soft feces was observed in all groups as well as decreased food comsumption and increased body temperature, in both cases (5-7 days after treatment); there was swelling of the infused leg in three of the animals receiving the bisantrene hydrochloride whereas this did not occur in animals receiving the bisantrene emulsion.

Figure 6:
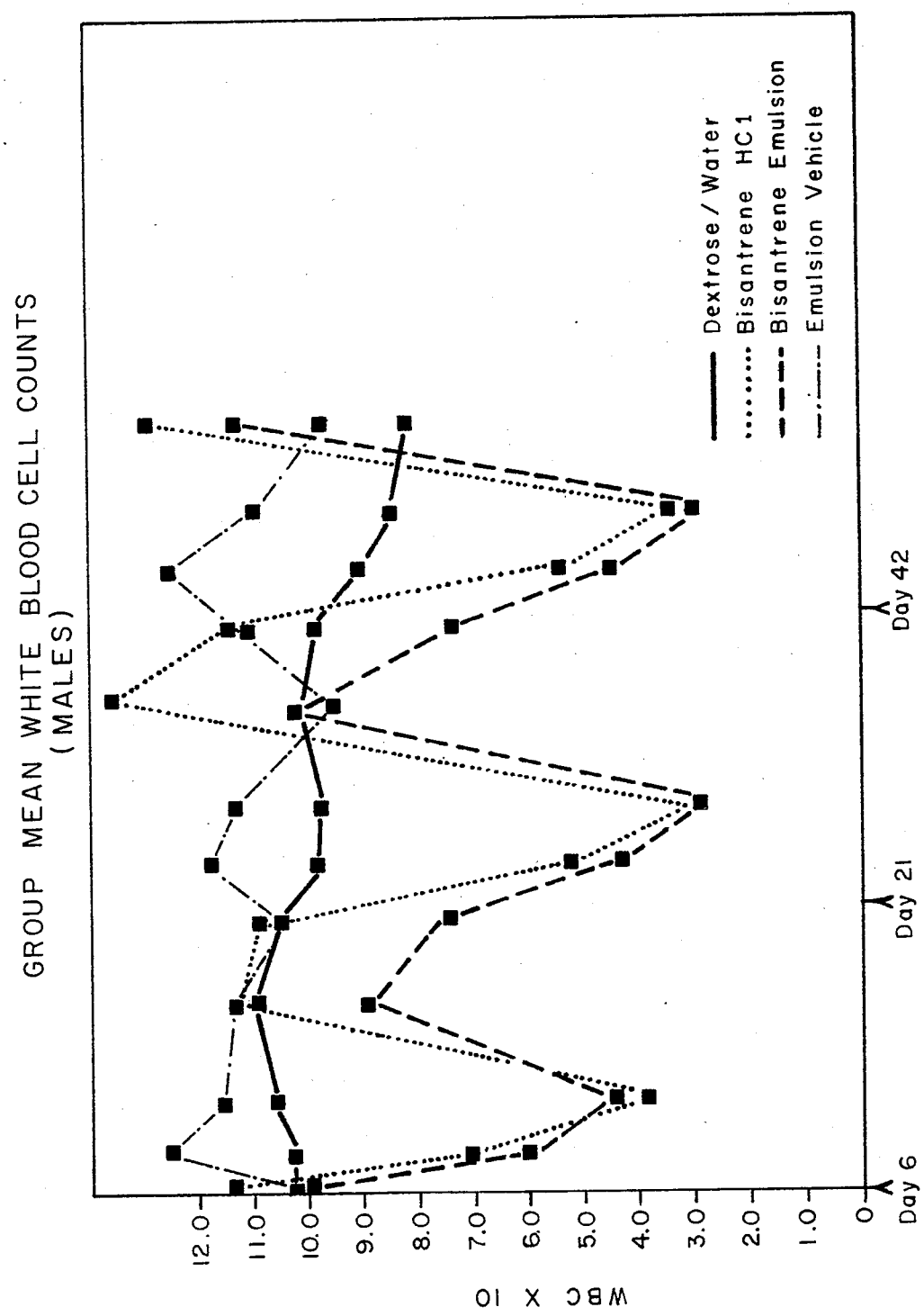
FIG. 6 is a plot of group mean white white blood cell counts (males).
Figure 7:
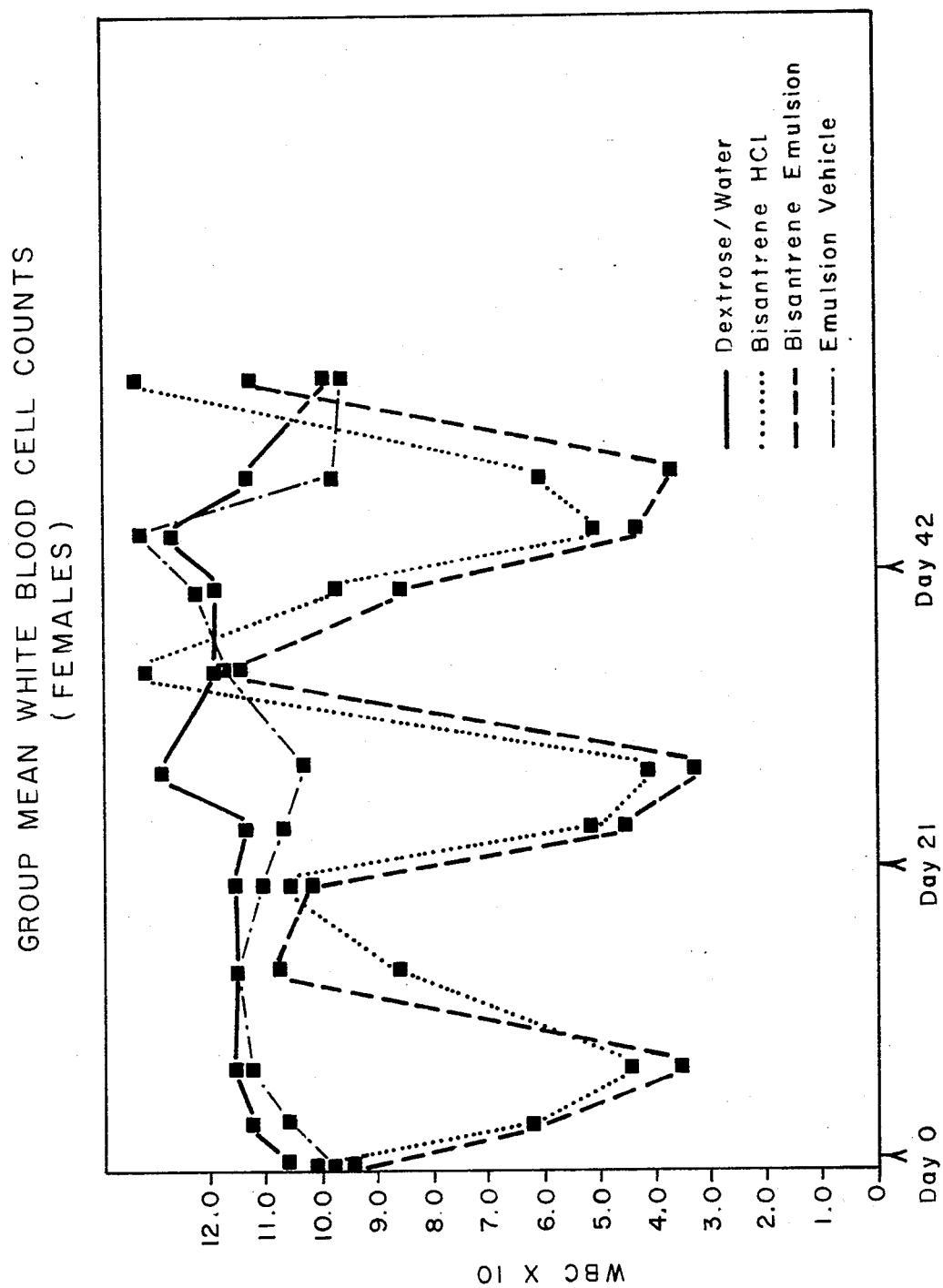
FIG. 7 is a plot of group mean white blood cell counts (females).

A comparison study of the group mean white blood cell counts (WBC$\times 10^{-3}$) was conducted separately for both the male and female animals in each group. The WBC counts of all animals were performed 7 days before dosing. Doses were administered on days 0, 21 and 42, whereas additional WBC counts on all animals were made on days 3, 7, 14, 20, 24, 28, 35, 41, 45, 49 and 56. The mean data from this test are recorded in Table VI and the group mean white blood cell counts for males and females are plotted separately in FIGS. 6 and 7 respectively.

TABLE VI

Bisantrene Formulations Comparison Study (WBC $\times 10^{-3}$)

| Treatment | Sex | −7 | 3 | 7 | 14 | 20 | 24 | 28 | 35 | 41 | 45 | 49 | 56 |
|---|---|---|---|---|---|---|---|---|---|---|---|---|---|
| 5% Dextrose | M | 10.2 | 10.2 | 10.5 | 10.9 | 10.5 | 9.8 | 9.7 | 10.0 | 9.8 | 9.0 | 8.4 | 8.5 |
|  | F | 10.6 | 11.2 | 11.5 | 11.5 | 11.5 | 11.2 | 12.8 | 11.8 | 11.7 | 12.7 | 11.1 | 9.9 |
| Bisantrene | M | 11.3 | 7.0 | 3.7 | 11.1 | 10.8 | 5.1 | 2.9 | 13.5 | 11.3 | 5.3 | 3.3 | 12.8 |
| HCl | F | 10.1 | 6.3 | 4.5 | 8.6 | 10.5 | 5.1 | 4.1 | 13.0 | 9.7 | 5.1 | 6.0 | 13.2 |
| Emulsion | M | 9.3 | 12.5 | 11.5 | 11.2 | 10.4 | 11.8 | 11.2 | 9.4 | 11.1 | 12.4 | 10.9 | 9.6 |
| Vehicle | F | 9.8 | 10.6 | 11.2 | 11.6 | 10.9 | 10.4 | 10.2 | 11.5 | 12.0 | 13.3 | 9.6 | 9.4 |
| Bisantrene | M | 10.0 | 6.0 | 4.2 | 8.9 | 7.3 | 4.2 | 2.8 | 10.1 | 7.2 | 4.4 | 2.8 | 11.2 |
| Emulsion | F | 9.4 | 6.2 | 3.5 | 10.7 | 10.1 | 4.5 | 3.3 | 11.4 | 8.5 | 4.3 | 3.6 | 11.1 |

When a comparison and evaluation of the data obtained in the preceding study was made it was concluded that local injection site deposits of the drug or binding of the drug of inflammation and phlebitis were absent for Bisantrene base in emulsion formulation and present for Bisantrene hydrochloride solution formulation. The white blood cell count nadir for bisantrene base emulsion was similar in magnitude and in time course to that of bisantrene hydrochloride in 5% dextrose/WFI. It was also concluded from the study that clinical signs attributable to bisantrene were similar for the two formulations while additional transient side effects were attributable to the emulsion vehicle in general and Emulphor EL-620P in particular.

Early formulations described in the present invention include Emulphor ® EL-620P as surfactant to stabilize the emulsion. In a few cases the literature indicates, at least in the dog model, that Emulphor ® or Cremaphor ® surfactants can cause histamine release type reactions such as, in mild cases, transient bodily rash, red spots near the eye or ear area and in severe cases anaphylactic responses. Later examples described in the present invention demonstrate that we were able to formulate stable emulsion with sparingly water soluble hydrophobic basic and/or acidic drugs for parenteral infusion without using these surfactants.

In the hereinbefore described study there was no noticeable effect of the bisantrene emulsion on lung or cardiovascular functions of the animals which were monitored by physical examination, EKG, blood pressure and X-ray.

What is claimed is:

1. A composition of matter for delivery by intravenous, intramuscular or intraarticular routes of hydrophobic drugs comprising:
   (a) a hydrophobic drug;
   (b) a pharmaceutically acceptable oleaginous vehicle or oil selected from the group consisting of (i) naturally occurring vegetable oils and (ii) semisynthetic mono, di or triglycerides said oil or oleaginous vehicle being free of BHT or BHA;
   (c) a surfactant or emulsifier;
   (d) a co-surfactant or auxiliary emulsifier;
   (e) an ion-pair former selected from $C_6-C_{20}$ saturated or unsaturated aliphatic or aromatic acids when the hydrophobic drug is basic and a pharamaceutically acceptable aliphatic or aromatic amine when the hydrophobic drug is acidic; and
   (f) water.

2. The composition of matter as recited in claim 1 comprising:

| Ingredient | Percent Range W/V |
|---|---|
| Basic Hydrophobic Drug | 0.01-5.0 |
| Soybean Oil | 3.0-20.0 |
| Sesame Oil (super-refined) | 0.0-5.0 |
| Oleic Acid N.F. | 0.2-4.0 |
| Hexanoic Acid ~short or long chain fatty acid to form an ion-pair | 0.0-0.50 |
| Polyvinylpyrrolidone | 0.0-0.2 |
| Soy or Egg Lecithin-emulsifier | 0.25-2.0 |
| Polyoxyethylated hydrocarbon | 0.0-1.0 |
| dl-α-Tocopherol | 0.0-0.05 |
| Glycerine U.S.P. | 0.5-2.25 |
| Water qs ad | 100 | wherein the hydrophobic drug comprises a sparingly water soluble ionizable solid or a water insoluble viscous oily liquid and/or comprises a basic drug which has a pK' lower or nearer the physiological pH or an acidic drug which has a pK' higher or nearer the physiological pH.

3. The composition of matter as recited in claim 1 comprising:

| Ingredient | Percent Range W/V |
|---|---|
| Acidic Hydrophobic Drug | 0.01-5.0 |
| N—Methyl-D-glucamine or R—NH—CH$_2$(CHOH)$_4$CH$_2$OH where R is alkyl(C$_1$-C$_6$) | 0.1-5.0 |
| Soybean Oil | 3.0-20.0 |
| Soy or Egg Lecithin | 0.2-2.0 |
| Benzyl Alcohol | 0.1-1.0 |
| Glycerine U.S.P. | 0.5-5.0 |

| Ingredient | Percent Range W/V |
|---|---|
| Water for Injection | qs | wherein the hydrophobic drug may be a sparingly water soluble ionizable solid or a water insoluble viscous oily liquid and/or may be an acidic drug which has an ionization constant higher or nearer the physiological pH.

4. The composition of matter as recited in claim 2 where the hydrophobic drug is bis(2-imidazolin-2-ylhydrazone)-9,10-anthracenedicarboxaldehyde.

5. The composition of matter as recited in claim 2 where the hydrophobic drug is 3-[4,6-bis[(1,1-2,2-tetramethylpropyl)amino]-s-triazin-2-yl]-3-azabicyclo[3.2.2]nonane.

6. The composition of matter as recited in claim 3 where the hydrophobic drug is 4-biphenyl acetic acid.

7. The composition of matter as recited in claim 1 comprising:

| Ingredient | Amount % W/V |
|---|---|
| Hydrophobic Drug | 0.2 |
| Soybean Oil | 10.0 |
| Oleic Acid N.F. | 1.2 |
| Soy Lecithin 95% P.C. | 1.2 |
| Polyoxyethylated hydrocarbon | 1.0 |
| dl-α-Tocopherol | 0.01 |
| Glycerine U.S.P. | 2.25 |
| Water qs ad | 100 |

8. The composition of matter as recited in claim 1 comprising:

| Ingredient | Amount % W/V |
|---|---|
| Hydrophobic Drug | 0.2 |
| Oleic Acid U.S.P. | 0.8 |
| Hexanoic Acid | 0.1 |
| Soybean Oil | 10.0 |
| Soy Lecithin 95% P.C. | 1.2 |
| dl-α-Tocopherol U.S.P. | 0.01 |
| Polyvinylpyrrolidone | 0.1 |
| Glycerine U.S.P. | 2.25 |
| Water qs ad | 100 |

9. The composition of matter as recited in claim 1 comprising:

| Ingredient | Percent W/V |
|---|---|
| Hydrophobic Drug | 1.0 |
| N—Methyl-D-glucamine | 0.92 |
| Soybean Oil | 7.00 |
| Soy Lecithin 95% P.C. | 1.00 |
| Benzyl Alcohol | 0.60 |
| Glycerine U.S.P. | 4.50 |
| Water qs ad | 100. |

10. The composition of matter as recited in claim 7 where the hydrophobic drug is bis(2-imidazolin-2-ylhydrazone)-9,10-anthracenedicarboxaldehyde.

11. The composition of matter as recited in claim 8 where the hydrophobic drug is bis(2-imidazolin-2-ylhydrazone)-9,10-anthracenedicarboxaldehyde.

12. The composition of matter as recited in claim 9 where the hydrophobic drug is 4-biphenyl acetic acid.

13. The composition of matter as recited in claim 1 comprising:

| Ingredient | Percent Range W/V |
|---|---|
| Hydrophobic Drug | 0.1–1.0 |
| Soybean Oil | 20.0 |
| Oleic Acid N.F. | 1.2 |
| Soy Lecithin 95% P.C. | 1.2 |
| Polyoxyethylated hydrocarbon | 1.0 |
| dl-α-Tocopherol U.S.P. | 0.01 |
| Water qs ad | 100 |

14. The composition of matter as recited in claim 3 where the hydrophobic drug is 3-[4,6-bis[(1,1-2,2-tetramethylpropyl)amino]-s-triazin-2-yl]-3-azabicyclo[3.2.2]-nonane.

15. The composition of matter as recited in claim 1, which consists essentially of:

| Ingredient | Percent W/V |
|---|---|
| Hydrophobic Drug | 0.2 |
| Soybean Oil | 10.0 |
| Oleic Acid N.F. | 1.2 |
| Soy Lecithin 95% P.C. | 1.2 |
| Polyoxyethylated Hydrocarbon | 1.0 |
| dl-α-Tocopherol | 0.01 |
| Glycerine U.S.P. | 2.25 |
| Water qs ad | 100. |

16. The composition of matter as recited in claim 1, which consists essentially of:

| Ingredient | Amount % W/V |
|---|---|
| Hydrophobic Drug | 0.2 |
| Oleic Acid U.S.P. | 0.8 |
| Hexanoic Acid | 0.1 |
| Soybean Oil | 10.0 |
| Soy Lecithin 95% P.C. | 1.2 |
| dl-α-Tocopherol U.S.P. | 0.01 |
| Polyvinylpyrrolidone Type N.P.-K-30 | 0.1 |
| Glycerine U.S.P. | 2.25 |
| Water qs ad | 100. |

17. The composition of matter as recited in claim 1, which consists essentially of:

| Ingredient | Percent W/V |
|---|---|
| Hydrophobic Drug | 1.0 |
| N—Methyl-D-glucamine | 0.92 |
| Soybean Oil | 7.00 |
| Soy Lecithin 95% P.C. | 1.00 |
| Benzyl Alcohol | 0.60 |
| Glycerine U.S.P. | 4.50 |
| Water qs ad | 100. |

18. The composition of matter as recited in claim 1, which consists essentially of:

| Ingredient | Percent Range W/V |
|---|---|
| Hydrophobic Drug | 0.1–1.0 |
| Soybean Oil | 20.0 |
| Oleic Acid N.F. | 1.2 |
| Soy Lecithin 95% P.C. | 1.2 |
| Polyoxyethylated Hydrocarbon | 1.0 |
| dl-α-Tocopherol | 0.01 |
| Water qs ad | 100. |

19. A composition as defined in claim 15, wherein the hydrophobic drug is bis(2-imidazolin-2-ylhydrazone)-9,10-anthracenedicarboxaldehyde.

20. A composition ad defined in claim 16, wherein the hydrophobic drug is bis(2-imidazolin-2-ylhydrazone)-9,10-anthracenedicarboxaldehyde.

21. A composition ad defined in claim 17, wherein the hydrophobic drug is bis(2-imidazolin-2-ylhydrazone)-9,10-anthracenedicarboxaldehyde.

22. A composition ad defined in claim 18, wherein the hydrophobic drug is bis(2-imidazolin-2-ylhydrazone)-9,10-anthracenedicarboxaldehyde.

* * * * *